(12) United States Patent
Ostraat et al.

(10) Patent No.: US 10,010,870 B2
(45) Date of Patent: Jul. 3, 2018

(54) SYNTHESIS OF CATALYTIC MATERIALS FOR METATHESIS AND ISOMERIZATION REACTIONS AND OTHER CATALYTIC APPLICATIONS VIA WELL CONTROLLED AEROSOL PROCESSING

(71) Applicant: Saudi Arabian Oil Company, Dhahran (SA)

(72) Inventors: Michele L. Ostraat, Cambridge, MA (US); Brian S. Hanna, Somerville, MA (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/252,733

(22) Filed: Aug. 31, 2016

(65) Prior Publication Data

US 2017/0136445 A1 May 18, 2017

Related U.S. Application Data

(60) Provisional application No. 62/254,425, filed on Nov. 12, 2015.

(51) Int. Cl.
*B01J 21/04* (2006.01)
*B01J 23/30* (2006.01)
(Continued)

(52) U.S. Cl.
CPC ............... *B01J 23/30* (2013.01); *B01J 21/08* (2013.01); *B01J 21/12* (2013.01); *B01J 35/1014* (2013.01);
(Continued)

(58) Field of Classification Search
CPC ... B01J 23/30; B01J 21/08; B01J 21/04; B01J 21/12; B01J 37/0201; B01J 37/0236;
(Continued)

(56) References Cited

U.S. PATENT DOCUMENTS 3,645,684 A  2/1972 De Cuir
3,865,751 A * 2/1975 Banks .................. C07C 6/04
                                                          502/251
(Continued)

FOREIGN PATENT DOCUMENTS

WO   2005016823 A1   2/2005
WO   2016061262 A1   4/2016

OTHER PUBLICATIONS

Hyeon-Lee et al., "Fractal Analysis of Flame-Synthesized Nanostructured Silica and Titania Powders Using Small-Angle X-Ray Scattering", Langmuir 1998, 5751-5756, 14, American Chemical Society/.

(Continued)

*Primary Examiner* — Patricia L. Hailey
(74) *Attorney, Agent, or Firm* — Dinsmore & Shohl LLP (57) ABSTRACT

Embodiments of a method of synthesizing a metathesis and isomerization catalyst or metathesis catalyst or isomerization catalyst comprises forming a catalyst precursor solution comprising a diluent and a catalyst precursor where the catalyst precursor comprises at least one of a silica precursor and an alumina precursor for the isomerization catalyst and additionally an oxometallate precursor or metal oxide precursor for the metathesis catalyst or the metathesis and isomerization catalyst, where the catalyst precursor solution is absent a surfactant; aerosolizing the catalyst precursor solution; drying the aerosolized catalyst precursor mixture to form a dried catalyst precursor; and reacting the dried catalyst precursor to yield the metathesis and isomerization catalyst or the metathesis catalyst or the isomerization catalyst, the metathesis and isomerization catalyst comprising a silica and alumina support with an oxometallate or a metal oxide distributed within the silica and alumina support.

22 Claims, 2 Drawing Sheets

(51) Int. Cl.

| | |
|---|---|
| *B01J 21/12* | (2006.01) |
| *B01J 21/08* | (2006.01) |
| *B01J 37/02* | (2006.01) |
| *B01J 35/10* | (2006.01) |
| *B01J 37/08* | (2006.01) |
| *C07C 6/04* | (2006.01) |
| *C07C 5/22* | (2006.01) |
| *B01J 37/00* | (2006.01) |
| *C07C 5/25* | (2006.01) |

(52) U.S. Cl.
CPC ....... *B01J 35/1019* (2013.01); *B01J 35/1023* (2013.01); *B01J 37/0045* (2013.01); *B01J 37/0201* (2013.01); *B01J 37/0236* (2013.01); *B01J 37/08* (2013.01); *C07C 5/2213* (2013.01); *C07C 5/2512* (2013.01); *C07C 6/04* (2013.01); *C07C 2521/08* (2013.01); *C07C 2521/12* (2013.01); *C07C 2523/30* (2013.01)

(58) Field of Classification Search
CPC .. B01J 37/08; C07C 2521/08; C07C 2521/12; C07C 2523/30
USPC .......................................................... 502/304
See application file for complete search history.

(56) References Cited

U.S. PATENT DOCUMENTS

| | | | | |
|---|---|---|---|---|
| 3,928,177 | A * | 12/1975 | Hayes | B01J 23/6527 208/111.1 |
| 4,575,575 | A * | 3/1986 | Drake | B01J 23/30 585/646 |
| 4,684,760 | A | 8/1987 | Drake | |
| 5,204,088 | A | 4/1993 | Noebel et al. | |
| 5,304,692 | A * | 4/1994 | Yamada | B01J 23/30 585/643 |
| 5,340,560 | A | 8/1994 | Rohr et al. | |
| 6,551,567 | B2 | 4/2003 | Konya et al. | |
| 6,586,785 | B2 | 7/2003 | Flagan et al. | |
| 6,723,606 | B2 | 4/2004 | Flagan et al. | |
| 6,780,805 | B2 | 8/2004 | Faber et al. | |
| 8,097,555 | B2 | 1/2012 | Costa et al. | |
| 8,246,933 | B2 | 8/2012 | Jiang et al. | |
| 8,415,267 | B2 | 4/2013 | Lee | |
| 8,440,874 | B2 | 5/2013 | Ramachandran et al. | |
| 8,895,795 | B2 | 11/2014 | Krawezyk et al. | |
| 9,586,198 | B2 | 3/2017 | Park et al. | |
| 9,682,367 | B2 | 6/2017 | Ali et al. | |
| 2005/0118096 | A1 | 6/2005 | Robson et al. | |
| 2008/0011876 | A1 | 1/2008 | Ostraat | |
| 2010/0056839 | A1* | 3/2010 | Ramachandran | B01J 23/007 585/646 |
| 2010/0286432 | A1 | 11/2010 | Tateno et al. | |
| 2011/0077444 | A1 | 3/2011 | Butler | |
| 2011/0092757 | A1 | 4/2011 | Akagishi et al. | |
| 2012/0016172 | A1* | 1/2012 | Miyazoe | B01J 23/002 585/670 |
| 2012/0039782 | A1 | 2/2012 | Nicholas | |
| 2017/0001925 | A1 | 1/2017 | Abudawound et al. | |
| 2017/0136445 | A1 | 5/2017 | Ostraat et al. | |

OTHER PUBLICATIONS

Keskinen et al., "On-Line Characterization of Morphology and Water Adsorption on Fumed Silica Nanoparticles", Aerosol Science and Technology, 2011, 1441-1447, 45, American Association for Aerosol Research.

Lin et al., "Aersol Processing of Low-Cost Mesoporous Silica Spherical Particles from Photonic Industrial Waste Powder for C02 Capture", Chemical Engineering Journal, 2012, 215-222, 197, Elsevier B.V.

Lu et al., "Aerosol-Assisted Self-Assembly of Mesostructured Spherical Nanoparticles", Nature, 1999, vol. 398, Macmillan Magazines Ltd.

International Search Report and Written Opinion for serial No. PCT/US2017/030014, dated Jul. 11, 2017.

Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 467, 224-234, Elsevier.

Bhuiyan et al., "Kinetics Modelling of 2-Butene Metathesis over Tungsten Oxide Containing Mesoporous Silica Catalyst", The Canadian Journal of Chemical Engineering, 2014, 92, 1271-1282, Canadian Society for Chemical Engineering.

Debecker et al., "Aerosol Route to Nanostructured WO3—SiO2—Al2O3 Metathesis Catalysts: Toward Higher Propene Yield", Applied Catalysis A: General, 2014, 470, 458-466, Elsevier.

Debecker et al., "Flame-Made MoO3/SiO2—Al2o3 Metathesis Catalysts with highly Dispersed and Highly Active Molybdate Species", Journal of Catalysis, 2011, 277, 154-163, Elsevier.

Bukhovko et al., "Continuous Aerosol Flow Reactors for the Controlled Synthesis of heterogeneous Catalyst Particles", AlChE Annual Meeting, Nov. 8-13, 2015.

Debecker et al., "A Non-Hydrolytic Sol-Gel Route to Highly Active MoO2—SiO2—Al2O3 metathesis Catalysts", Catalysis Science & Technology, 2012, 2:6, 1075-1294, RSC Publishing.

Liu et al., "Alumina with Various pore Structures Prepared by Spray Pyrolysis of Inorganic Aluminum Precursors", I&EC Research, 2013, 52, 13377-13383, ACS Publications.

Maksasithorn, Surasa et al., "Preparation of super-microporous WO3—SiO2 olefin metathesis catalysts by the aerosol-assisted sol-gel process", pp. 125-133, Microporous and Mesoporous Materials 213 (2015).

International Search Report and Written Opinion pertaining to PCT/US2016/060258 dated Mar. 7, 2017.

Ishihara et al., "Hydrocracking of 1-methylnaphthalene/decahydronaphthalene mixture catalyzed by zeolite-alumina composite supported NiMo catalysts", Fuel Processing Technology 116, pp. 222-227, 2013.

Xie et al., "An Overview of Recent Development in Composite Catalysts from Porous Materials for Various Reactions and Processes", Int. J. Mol. Sci. 11, pp. 2152-2187, 2010.

Notice of Allowance pertaining to U.S. Appl. No. 15/146,037, filed May 4, 2016, 8 pages.

* cited by examiner

SYNTHESIS OF CATALYTIC MATERIALS FOR METATHESIS AND ISOMERIZATION REACTIONS AND OTHER CATALYTIC APPLICATIONS VIA WELL CONTROLLED AEROSOL PROCESSING

CROSS-REFERENCE TO RELATED APPLICATIONS

This application claims priority to U.S. Provisional Patent Application No. 62/254,425 filed Nov. 12, 2015, which is incorporated by reference herein in its entirety.

TECHNICAL FIELD

Embodiments of the present disclosure generally relate to synthesis of metathesis and isomerization catalytic materials, and more specifically relate to the synthesis of catalysts via aerosol processing with metathesis and isomerization, metathesis, or isomerization functionalities.

BACKGROUND

In recent years, there has been a dramatic increase in the demand for propylene to feed the growing markets for polypropylene, propylene oxide and acrylic acid. Currently, most of the propylene produced worldwide (74 million tons/year) is a by-product from steam cracking units (57%) which primarily produce ethylene, or a by-product from Fluid Catalytic Cracking (FCC) units (30%) which primarily produce gasoline. These processes cannot respond adequately to a rapid increase in propylene demand.

Raffinate is the residue C4 stream from a naphtha cracking process or from a gas cracking process when components are removed (the C4 stream typically containing, as its chief components, n-butane, 1-butene, 2-butene, isobutene and 1,3-butadiene, and optionally some isobutane and said chief components together forming up to 99% or more of the C4 stream). Specifically, Raffinate-2 is the C4 residual obtained after separation of 1,3-butadiene and isobutylene from the C4 raffinate stream and consists mainly of cis- or trans-2-butene, 1-butene, and n-butane. Similarly, Raffinate-3 is the C4 residual obtained after separation of 1,3-butadiene, isobutylene, and 1-butene from the C4 raffinate stream and consists mainly of cis- or trans-2-butene, n-butane, and unseparated 1-butene. Utilizing Raffinate-2 and Raffinate 3 streams for conversion to propylene is desirable to increase the available supply of propylene.

Development of a metathesis catalyst necessary to convert Raffinate-2 and Raffinate 3 streams have relied on wet impregnation or grafting techniques to insert a metal oxide into a previously synthesized support material. However, wet impregnation or grafting techniques are limited in that the entire particle volume of the catalyst is not always accessible for insertion of a metal oxide and control of the properties of the resulting metathesis catalyst is limited.

SUMMARY

Accordingly, ongoing needs exist for improved methods of synthesis of metathesis and isomerization catalysts. Embodiments of the present disclosure are directed to synthesis of metathesis and isomerization catalysts via an aerosol processing regimen.

In one embodiment, a method of synthesizing a metathesis and isomerization catalyst is provided. The method comprises forming a catalyst precursor mixture comprising a diluent and a catalyst precursor, the catalyst precursor comprising an oxometallate precursor and at least one of an alumina precursor and a silica precursor, where the catalyst precursor mixture is absent a surfactant. The method further comprises aerosolizing the catalyst precursor mixture and drying the aerosolized catalyst precursor mixture to form a dried catalyst precursor. Further, the method includes reacting the dried catalyst precursor to yield the metathesis and isomerization catalyst. The metathesis and isomerization catalyst comprises a silica or silica and alumina support with an oxometallate distributed within the silica or silica and alumina support.

In another embodiment, a method of synthesizing a metathesis and isomerization catalyst is provided. The method comprises forming a catalyst precursor mixture comprising a diluent and a catalyst precursor, the catalyst precursor comprising a metal oxide precursor and at least one of an alumina precursor and a silica precursor, where the catalyst precursor mixture is absent a surfactant. The method further comprises aerosolizing the catalyst precursor mixture and drying the aerosolized catalyst precursor mixture to form a dried catalyst precursor. Further, the method includes reacting the dried catalyst precursor to yield the metathesis and isomerization catalyst. The metathesis and isomerization catalyst comprises a silica or silica and alumina support with a metal oxide distributed within the silica or silica and alumina support.

In another embodiment, a method of synthesizing an isomerization catalyst is provided. The method comprises forming a catalyst precursor mixture comprising a diluent and a catalyst precursor, the catalyst precursor comprising a silica precursor and an alumina precursor, where the catalyst precursor solution is absent a surfactant. The method further includes aerosolizing the catalyst precursor mixture and drying the aerosolized catalyst precursor mixture to form a dried catalyst precursor. Further, the method includes reacting the dried catalyst precursor to yield the isomerization catalyst, the isomerization catalyst comprising a silica and alumina support.

In yet another embodiment, a method of synthesizing a metathesis catalyst is provided. The method comprises forming a catalyst precursor mixture comprising a diluent and a catalyst precursor, the catalyst precursor comprising an oxometallate precursor or a metal oxide precursor and at least one of an alumina precursor and a silica precursor, where the catalyst precursor mixture is absent a surfactant. The method further includes aerosolizing the catalyst precursor mixture and drying the aerosolized catalyst precursor mixture to form a dried catalyst precursor. Further, the method includes reacting the dried catalyst precursor to yield the metathesis catalyst, the metathesis catalyst comprising a silica or silica and alumina support with an oxometallate or metal oxide distributed within the silica or silica and alumina support.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Embodiments of the present disclosure are directed to methods of synthesizing metathesis and isomerization catalysts, metathesis catalysts, and isomerization catalysts. Specifically, the present embodiments are related to synthesizing a metathesis and isomerization catalyst, an isomerization catalyst, or a metathesis catalyst via an aerosolization process.

Throughout this disclosure, conversion of 2-butene to propylene via utilization of the metathesis and isomerization catalyst is described; however it should be understood that this is merely for clarity and conciseness and other metathesis reactions are similarly envisioned.

Synthesizing a metathesis and isomerization catalyst, a metathesis catalyst, or an isomerization catalyst in accordance with at least one embodiment of this disclosure includes forming a catalyst precursor mixture, aerosolizing the catalyst precursor mixture, drying the aerosolized catalyst precursor mixture to form a dried catalyst precursor, and reacting the dried catalyst precursor to yield the metathesis and isomerization catalyst, the metathesis catalyst, or the isomerization catalyst.

The metathesis and isomerization catalyst or metathesis catalyst comprises a silica and alumina support with an oxometallate or metal oxide distributed within the silica and alumina support. The silica and alumina support as well as the oxometallate or metal oxide distributed within the silica and alumina support participate in the isomerization of 2-butene. The oxometallate or metal oxide distributed within the silica and alumina support is responsible for the metathesis portion of the reaction. Both functionalities can be controlled independently for a variety of desired reactions through the use of various metal precursors forming the oxometallate or metal oxide distributed within the silica and alumina support and dopants in the catalyst precursor mixture.

The catalyst precursor mixture comprises a catalyst precursor and a diluent. In one or more embodiments, the catalyst precursor comprises an oxometallate precursor and at least one of an alumina precursor and a silica precursor. In further embodiments, the catalyst precursor comprises a metal oxide precursor and at least one of an alumina precursor and a silica precursor.

Throughout this disclosure reference is made to the metathesis and isomerization catalyst; however it should be understood that this is merely for conciseness and a metathesis catalyst alone or an isomerization catalyst alone may be generated in accordance with the methods of this disclosure. Specifically, omitting the oxometallate and metal oxide precursor from the catalyst precursor mixture results in the isomerization catalyst alone. Similarly, adjusting the chemistry of the silica precursor and the alumina precursor results in a silica-alumina support for the oxometallate or metal oxide without an isomerization functionality to generate the metathesis catalyst alone.

In one or more embodiments the silica precursor comprises fumed silica. In various other embodiments, the silica precursor comprises colloidal silica, silane ($SiH_4$), silicon tetrachloride, or tetraethyl orthosilicate (TEOS).

In one or more embodiments the alumina precursor comprises aluminum nitrate ($Al(NO_3)_3$). In various other embodiments, the alumina precursor comprises fumed alumina or additional aluminum salts and their hydrates, such as $AlCl_3$, $AlPO_4$, or $Al_2(SO_4)_3$.

In various embodiments, the oxometallate precursor comprises a tungstate precursor. In one or more embodiments the tungstate precursor comprises ammonium metatungstate (($NH_4)_6H_2W_{12}O_{40}$). In various other embodiments, the tungstate precursor comprises tungstic acid, phosphotungstic acid, or sodium tungstate.

In various embodiments the metal oxide precursor comprises a precursor of one or more oxides of a metal from the Groups 6-10 of the IUPAC Periodic Table. In one or more embodiments, the metal oxide may be an oxide of rhenium, tungsten, cerium, or combinations thereof. In a specific embodiment, the metal oxide is tungsten oxide ($WO_3$).

In various embodiments, the diluent is water or an organic solvent. Example organic solvents include methanol, ethanol, acetone, or a combination of solvents. In embodiments with water as the diluent, an aqueous catalyst precursor mixture is formed.

In embodiments the catalyst precursor solution is absent a surfactant. Without wishing to be bound by theory, the catalyst precursor mixture forms the metathesis and isomerization catalyst without the support and assistance of a surfactant.

In one or more embodiments the catalyst precursor comprises 0.1 to 99.9 weight % (wt. %) silica precursor, 0.1 to 20 wt. % oxometallate precursor or metal oxide precursor, and 0.0 to 99.8 wt. % alumina precursor. In further embodiments, the catalyst precursor comprises 8 to 12 wt. % oxometallate precursor or metal oxide precursor with the silica precursor and alumina precursor each comprising the remaining 0.1 to 92 wt. %. In further embodiments the catalyst precursor comprises 75.0 to 99.9 wt. % silica precursor, 0.1 to 20 wt. % oxometallate precursor or metal oxide precursor, and 0.0 to 5.0 wt. % alumina precursor. It is contemplated that various amounts of metal oxide or oxometallate may be present in the synthesized metathesis and isomerization catalyst. For example, and not by way of limitation, the weight ratio of silica to metal oxide, for example, $WO_3$, may be about 5:1 to about 60:1, or about 5:1 to about 15:1, or about 20:1 to about 50:1, or about 20:1 to about 40:1, or about 25:1 to about 35:1.

The catalyst precursor mixture may be formed as a solution or as a suspension. For example, with fumed precursors or colloidal precursors, a suspension is formed for the catalyst precursor mixture. However, for precursors comprising metal salts, a solution is formed.

The catalyst precursor mixture is aerosolized to form an aerosolized mixture of the catalyst precursor mixture. In one or more embodiments the catalyst precursor mixture is aerosolized in a nebulizing unit. A variety of nebulizing units are envisioned, as long as they generate a liquid spray. Examples of nebulizing units include ultrasonic transducers and spray nozzles. One non-limiting benefit of an ultrasonic transducer is that it is readily scalable and highly controllable.

Aerosol processing overcomes deficiencies in previous methods of forming a metathesis catalyst. Specifically, using a wet impregnation or grafting technique to infuse a metal oxide into a support structure has inherent limitations. The support materials must be synthesized in a separate step with infusion of a metal oxide or other desired species requiring secondary processing. Further, accessibility of the entire particle volume is not always possible with a wet impregnation or grafting technique. Conversely, with aerosol processing, the metal oxide or other desired species is entrained during initial processing and is naturally able to be diffused throughout the entire particle volume or to be strategically concentrated on the surface of the particle.

Prior to aerosolizing the catalyst precursor, the catalyst precursor is combined with the diluent to form the catalyst precursor mixture. In one or more embodiments, the catalyst precursor mixture is aerosolized at a catalyst precursor concentration of between 1 wt. % and 20 wt. %. In various further embodiments, the catalyst precursor is combined with water and aerosolized at a catalyst precursor concentration of between 1 wt. % and 6 wt. %, between 2 wt. % and 5 wt. %, or between 2 wt. % and 4 wt. %.

In one or more embodiments, a carrier gas may transport the aerosolized catalyst precursor mixture into a heated furnace for drying of the aerosolized catalyst precursor. In one or more embodiments, the carrier gas is air. In various additional embodiments, the carrier gas comprises nitrogen, argon, helium, or mixtures of multiple gases. In yet further embodiments, the carrier gas may be a reactant for the formation of the metathesis and isomerization catalyst, the metathesis catalyst, or the isomerization catalyst. For example, the carrier gas may be silane ($SiH_4$). The selection of a non-reactive gas or a reactive gas is dependent upon the precursors utilized and the desired metathesis and isomerization catalyst, metathesis catalyst, or isomerization catalyst to be formed.

Figure 1:
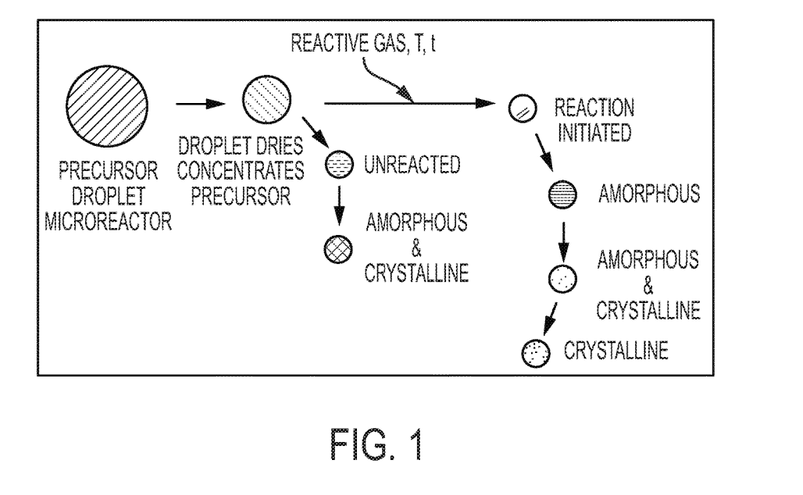
FIG. 1 is a flow diagram of the aerosol processing in accordance with one or more embodiments of the present disclosure.

The heated furnace dries the aerosolized catalyst precursor mixture and also has the potential to initiate formation of crystallinity within the metathesis and isomerization catalyst, metathesis catalyst, or isomerization catalyst formed from the dried aerosolized catalyst precursor. It is noted that the aerosolized catalyst precursor mixture need not be fully dried prior to initiation of crystallization. As illustrated in FIG. 1, droplets of the aerosolized catalyst precursor mixture start to dry and the catalyst precursor becomes more concentrated. Subsequently, during heating, the dried or partially dried catalyst precursor can react to form amorphous structures, crystalline structures, or a combination of amorphous and crystalline structures depending upon the catalyst precursor chemistry. In one or more embodiments the furnace is heated to between 500° C. and 1500° C. In further embodiments the furnace is heated to between 1000° C. and 1500° C. The elevated temperature results in the catalyst precursors reacting to form the desired products. In further embodiments, to merely dry the catalyst precursor mixture, the furnace is heated to between 100° C. and 800° C.

In one or more embodiments, the heated furnace comprises multiple temperature zones. The different temperature zones may operate at different temperatures. For example, a first temperature zone between 100° C. and 500° C. may be utilized to dry or partially dry the aerosolized catalyst precursor mixture, and a second temperature zone between 800° C. and 1500° C. may be utilized to react the catalyst precursors and form the desired products.

In one or more embodiments, the residence time in the heated furnace is between 0.1 and 10 seconds. If the residence time is of insufficient length the particles do not dry and may be left unreacted such that the final desired metathesis and isomerization catalyst, the final metathesis catalyst, or the final isomerization catalyst are not formed. Conversely, if the residence time is unnecessarily extended energy is wasted and the metathesis and isomerization catalyst particles, metathesis catalyst particles, or isomerization catalyst particles may be lost to the heated furnace tube walls. Additionally, too rapidly drying the aerosolized catalyst precursor mixture can lead to particle shells which can collapse with further processing opposed to solid catalyst particles.

The crystallinity of the metal oxide in the formed metathesis and isomerization catalyst or metathesis catalyst is dependent upon various factors including the oxometallate or metal oxide loading in the silica and alumina support. At low oxometallate or metal oxide loadings, such as 2-5 wt. %, there is no observable formation of crystallinity in the heated furnace. At higher loadings, such as 10-20 wt. %, there is observable crystallinity in the heated furnace with more crystallinity being observed at the higher end of the range. Post treatment of the metathesis and isomerization catalyst or metathesis catalyst collected from the heated furnace in air, such as calcination at 550° C., increases the overall crystallinity of the oxometallate or metal oxide.

Previous attempts at using a spray dryer for aerosol processing have been met with several limitations. Specifically, the temperature range for processing was limited to between the freezing point of the solution for processing and 220° C. Further, a conventional spray dryer setup is limited to two solutions being mixed at the reactor.

The feed rate of catalyst precursor into the heated furnace varies based on the flow rate of carrier gas. In general, the faster the flow rate of the carrier gas, the higher the feed rate of catalyst precursor into the heated furnace. However, the carrier gas flow rate also can impact residence time, with a higher carrier gas flow rate resulting in a reduced residence time. A balance must be reached to maximized production of metathesis and isomerization catalyst, metathesis catalyst, or isomerization catalyst through an increased flow rate of catalyst precursor without overly reducing the residence time in the heated furnace. In an ultrasonic transducer system, a carrier gas flow rate of 1.25 L/min/transducer to 3.75 L/min/transducer is a desirable range.

In one or more embodiments the method further comprises collecting the metathesis and isomerization catalyst, metathesis catalyst, or isomerization catalyst with a filter from the flow of the carrier gas exiting the heated furnace. An example filter comprises borosilicate fibers bound with polyvinylidene fluoride (PVDF) configured to have a 93% efficiency at capturing 0.01 μm particles. The filter may also be comprised of any typically commercially available bag house filter material. In selecting a filter there is a desire to balance pore size of the filter to sufficiently collect the catalyst particles with the resulting pressure increase which results as the filter collects catalyst particles. As the filter begins to clog and a particle cake forms, the filter becomes a more efficient filter and the pressure starts to rise. In operation, the resulting pressure rise may be used as an indicator of the quantity of metathesis and isomerization catalyst, metathesis catalyst, or isomerization catalyst collected within the filter.

As the water or other diluent is removed from the individual droplets of the aerosolized catalyst precursor solution the droplets become more concentrated.

In one or more embodiments the catalyst precursor comprises one or more dopants. Envisioned dopants include, but are not limited to, titania, rhenia, and phosphates. Synthesis of metathesis and isomerization catalysts, metathesis catalysts, or isomerization catalysts via an aerosolization scheme allows for the inclusion of dopants during initial processing and formation of the metathesis and isomerization catalyst, metathesis catalyst, or isomerization catalyst opposed to relying on post-processing addition. The dopant may be included as a constituent of the catalyst precursor solution and thus is entrained in-situ during aerosolization and standard formation of the metathesis and isomerization catalyst, the metathesis catalyst, or the isomerization catalyst.

In further embodiments, the method of synthesizing the metathesis and isomerization catalyst, the metathesis catalyst, or the isomerization catalyst may comprises aerosolizing a dopant stream concurrently with aerosolizing the catalyst precursor to yield the metathesis and isomerization catalyst, the metathesis catalyst, or the isomerization catalyst with dopants entrained in the silica and alumina support. In further embodiments, the dopant stream may be added after a first heated furnace and before a second heated furnace.

A metathesis reaction is a chemical process involving the exchange of bonds between two reacting chemical species, which results in the creation of products with similar or identical bonding affiliations. This reaction is represented by the general scheme in the following Formula 1.

$$A\text{-}B+C\text{-}D \rightarrow A\text{-}D+C\text{-}B \qquad \text{Formula 1:}$$

As shown in the following Formulas 2 and 3, "isomerization" and "metathesis" of 2-butene to propylene is generally a two-step process: 2-butene isomerization using an isomerization catalyst system and then cross-metathesis using a metathesis catalyst system. The 2-Butene Isomerization (Formula 2) may be achieved with both the silica and alumina support of the isomerization catalyst and the silica or silica and alumina support of the metathesis and isomerization catalyst. The Cross-Metathesis (Formula 3) may be achieved by the oxometallate or metal oxide of the metathesis and isomerization catalyst or the metathesis catalyst. The metathesis and isomerization catalyst provides both the "isomerization" and "metathesis" steps with each component of the isomerization and metathesis catalyst providing individual functionalities.

Formula 2: 2-Butene Isomerization

2-Butene             1-Butene Formula 3: Cross-Metathesis 2-Butene      1-Butene 1-Propene      2-Pentene Referring to Formulas 2 and 3, the "isomerization" and "metathesis" reaction is not limited to these reactants and products; however, Formulas 2 and 3 provide a basic illustration of the reaction methodology. As shown in Formula 3, metathesis reaction takes place between two alkenes. The groups bonded to the carbon atoms of the double bond are exchanged between the molecules to produce two new alkenes with the swapped groups. The specific catalyst that is selected for the olefin metathesis reaction may generally determine whether a cis-isomer or trans-isomer is formed, as the coordination of the olefin molecules with the catalyst play an important role, as do the steric influences of the substituents on the double bond of the newly formed molecule.

Control of the characteristics of the metathesis and isomerization catalyst, the metathesis catalyst, or the isomerization catalyst allows for the conversion of a variety of different chemicals. Varying the synthesis characteristics of the aerosolization process may allow the resulting metathesis and isomerization catalyst, metathesis catalyst, or isomerization catalyst to exhibit a range of structural and chemical properties which are optimized for differing conversion reactions. For example, adjusting the structural and chemical properties of the silica and alumina support may allow the isomerization functionality to be optimized and adjusting the properties of the oxometallate or metal oxide distributed within the silica and alumina support may allow the metathesis functionality to be optimized.

The composition of the metathesis and isomerization catalyst, the metathesis catalyst, or the isomerization catalyst may be controlled by changing the precursors, the selection and incorporation of carrier gas, and the relative concentrations of the precursors and carrier gas in the catalyst precursor solution. For example, inclusion of a higher relative concentration of one precursor in the catalyst precursor solution will result in a relatively higher concentration in the final metathesis and isomerization catalyst, the final metathesis catalyst, or the final isomerization catalyst. Additionally, oxometallates and metal oxides in the metathesis and isomerization catalyst or metathesis catalyst in accordance with the present disclosure may be generated using air as the carrier gas. Specifically, air comprises oxygen which can be incorporated into the resulting metathesis and isomerization catalyst or metathesis catalyst. Further, in embodiments with water as a diluent, oxygen from the heated water may also be used as an oxygen source.

The acidity of the metathesis and isomerization catalyst, the metathesis catalyst, or the isomerization catalyst may be controlled with the amount and selection of the alumina precursor in the catalyst precursor solution. Isomerization is affected by the acidity of the metathesis and isomerization catalyst or the isomerization catalyst. Acidity is controlled in at least two ways. First, the total number of acidic sites in the metathesis and isomerization catalyst or the isomerization catalyst is controlled by the amount of aluminum incorporated into the structure. The more aluminum sites that are present the more Al—OH will be present. Second, the acid strength is also affected by the aluminum sites and how they interact with the silica sites. The choice of catalyst precursors may have an effect on the formation of various sites. For example: fumed alumina has a large cluster of alumina already formed, therefore the interactions between the alumina and silica are largely predefined and limited to the interface of the two discrete materials. In the case of $Al(NO_3)_3$ the alumina that is created is a single molecule and can potentially interact with silica in all dimensions remaining isolated. Further, in various embodiments, the metathesis and isomerization catalyst, the metathesis catalyst, or the isomerization catalyst may have a total acidity of up to about 0.5 millimole/gram (mmol/g), or about 0.01 mmol/g to about 0.5 mmol/g, or about 0.1 mmol/g to about 0.5 mmol/g, or about 0.3 mmol/g to about 0.5 mmol/g, or about 0.4 mmol/g to about 0.5 mmol/g. It will be appreciated that in further embodiments the metathesis and isomerization catalyst, the metathesis catalyst, or the isomerization catalyst may have a total acidity below 0.01 mmol/g or above 0.5 mmol/g. Acidity of the catalyst is selected to yield the desired selectivity of propylene and reduced production of undesirable by-products such as aromatics. Increasing acidity may increase the overall butene conversion; however, this increased conversion may lead to less selectivity and increased production of aromatic by-products, which can lead to catalyst coking and deactivation.

The particle size of the metathesis and isomerization catalyst, the metathesis catalyst, or the isomerization catalyst may be controlled by adjusting the precursor concentration in the aerosolized catalyst precursor solution, the aerosolization method and specifications, and the reactor configuration. For example, a higher concentration of precursors relative to water or other diluent in the catalyst precursor solution results in larger particles as less water or other diluent is available to evaporate from each aerosolized droplet. Additionally, different aerosolization methods result in differing size droplets and thus differing particle sizes of the final metathesis and isomerization catalyst, the final metathesis catalyst, or the final isomerization catalyst. Changing the frequency in an ultrasonic nebulizer can impact the particle size of the metathesis and isomerization catalyst, the metathesis catalyst, or the isomerization catalyst as the droplet size of the catalyst precursor mixture will change at different frequencies. Increasing turbulent flow within the aerosolization unit or heated furnace can increase particle size as droplets collide and merge together. Similarly, impactors can separate larger wet droplets of the catalyst precursor mixture and only allow smaller droplets to enter the heated furnace resulting in smaller catalyst particle sizes. Furthermore, in various embodiments, the metathesis and isomerization catalyst, the metathesis catalyst, or the isomerization catalyst may have a particle size of from about 5 nm to about 4000 nm, or about 100 nm to about 2500 nm. In additional embodiments, the metathesis and isomerization catalyst, the metathesis catalyst, or the isomerization catalyst may be an aggregate comprised of primary particles with sizes of about 5 nm to 250 nm. These metathesis and isomerization catalysts, metathesis catalysts, or isomerization catalysts may be further granulated to 1 μm to about 100 μm, or about 10 μm to about 40 μm.

The surface area of the metathesis and isomerization catalyst, the metathesis catalyst, or the isomerization catalyst may be controlled by adjusting precursors, including inert and sacrificial constituents in the catalyst precursor solution, and adjusting the reactor configuration. Inert and sacrificial constituents may include polystyrene latex or NaCl, for example. When heated to high temperature, the polystyrene latex burns off, leaving pores where the polystyrene latex was previously. Similarly, with NaCl, once the metathesis and isomerization catalyst particle, the metathesis catalyst particle, or the isomerization catalyst particle is formed it may be placed in water and the NaCl dissolved away, leaving behind the non-NaCl particle structure. One having skill in the art will appreciate that other sacrificial continuants may be utilized which burn off at an elevated temperature or which are soluble in water or other solvent to result in a metathesis and isomerization catalyst, metathesis catalyst, or isomerization catalyst with the sacrificial constituent removed and an increased surface area. Further, selection of fumed silica and fumed alumina as precursors may result in an increased surface area. When aerosolized, the high fractal surface area of fumed silica and fumed alumina structures is generally preserved. This high fractal surface area results in an increased surface area when compared to non-fumed precursors which result in more spherical, dense particles, with lower surface area since they do not have much internal surface area. Moreover, while broader ranges are contemplated, the metathesis and isomerization catalyst, the metathesis catalyst, or the isomerization catalyst may, in one or more embodiments, include a surface area of about 100 meters²/gram ($m^2/g$) to about 700 $m^2/g$. In further embodiments, the metathesis and isomerization catalyst, the metathesis catalyst, or the isomerization catalyst may have a surface area of from about 450 $m^2/g$ to about 600 $m^2/g$, or about 250 $m^2/g$ to about 350 $m^2/g$, or about 275 $m^2/g$ to about 325 $m^2/g$, or about 275 $m^2/g$ to about 300 $m^2/g$.

The crystallinity of the metathesis and isomerization catalyst, the metathesis catalyst, or the isomerization catalyst may be controlled by adjusting the precursor selection, the heated furnace temperature, the furnace residence time, and the cooling rates of the metathesis and isomerization catalyst, the metathesis catalyst, or the isomerization catalyst. For example, a relatively slower cooling rate provides additional time for the crystal arrangement to occur, where a relatively faster cooling rate can lock atoms into metastable or amorphous states, which are not typically found at equilibrium. Regarding precursor selection, the use of a metal oxide or oxometallate source that contains a single metal center versus multiple metal centers can lead to more dispersion because the fracturing of the cluster is not required. The more metal centers the metal oxide or oxometallate source that contains the more fracturing that is required to form crystallinity. Regarding furnace temperature and residence time, at elevated temperatures or elongated times the metal oxides or oxometallates may migrate on the surface which allows for increased crystallite size.

Moreover, the pore size distribution of the metathesis and isomerization catalyst, the metathesis catalyst, or the isomerization catalyst in one or more embodiments range from about 2.5 nm to about 40 nm and a total pore volume of at least about 0.600 $cm^3/g$. Without being bound by theory, the present pore size distribution and pore volume are sized to achieve better catalytic activity and reduced blocking of pores by metal oxides, whereas smaller pore volume and pore size catalyst systems are susceptible to pore blocking and thereby reduced catalytic activity.

In one or more embodiments, the pore size distribution of the metathesis and isomerization catalyst, the metathesis catalyst, or the isomerization catalyst may range from about 2.5 nm to about 40 nm, or about 2.5 nm to about 20 nm, or about 2.5 nm to about 4.5 nm, or about 2.5 nm to about 3.5 nm, or about 8 nm to about 18 nm, or about 12 nm to about 18 nm. In further embodiments, the total pore volume may be from about 0.600 $cm^3/g$ to about 2.5 $cm^3/g$, or about 0.600 $cm^3/g$ to about 1.5 $cm^3/g$, or about 0.600 $cm^3/g$ to about 1.3 $cm^3/g$, or about 0.600 $cm^3/g$ to about 0.800 $cm^3/g$, or about 0.600 $cm^3/g$ to about 0.700 $cm^3/g$, or about 0.900 $cm^3/g$ to about 1.3 $cm^3/g$.

EXAMPLES

The following examples show the preparation of various metathesis and isomerization catalysts which were used for the synthesis of propylene at 550° C. in a fixed bed reactor from a stream of butene and nitrogen.

Example 1—Aerosolized 100% Silica with 2 wt. % $WO_3$ at 1400° C.

A precursor was prepared from 43.6 g fumed silica, 0.941 g ammonium metatungstate, and 726 milliliter (ml) water. The precursor was provided to an ultrasonic nebulizer at 21 milliliters per minute (ml/min) until aerosol flow was observed. Subsequently, the flow of precursor to the ultrasonic nebulizer was reduced to 1 ml/min for 120 min. The aerosolized precursor was transferred to a heated furnace at 1400° C. with a flow of air at 5 liters per minute (L/min).

Flow of air was continued for 120 min. Upon exit from the heated furnace, the formed metathesis and isomerization catalyst was collected in a filter. A total of 2059 milligram (mg) of metathesis and isomerization catalyst was collected.

Example 2—Aerosolized 100% Silica with 2 wt. % $WO_3$ at 1000° C.

A precursor was prepared from 43.6 g fumed silica, 0.941 g ammonium metatungstate, and 726 ml water. The precursor was provided to an ultrasonic nebulizer at 21 ml/min until aerosol flow was observed. Subsequently, the flow of precursor to the ultrasonic nebulizer was reduced to 1 ml/min for 120 min. The aerosolized precursor was transferred to a heated furnace at 1000° C. with a flow of air at 5 L/min. Flow of air was continued for 120 min. Upon exit from the heated furnace, the formed metathesis and isomerization catalyst was collected in a filter. A total of 1247 mg of metathesis and isomerization catalyst was collected.

Example 3—Aerosolized 100% Silica with 10 wt. % $WO_3$ (Wet Impregnation)

A precursor was prepared from 64 g fumed silica, and 1000 ml water. The precursor was provided to an ultrasonic nebulizer at 21 ml/min until aerosol flow was observed. Subsequently, the flow of precursor to the ultrasonic nebulizer was reduced to 1 ml/min for 120 min. The aerosolized precursor was transferred to a heated furnace at 1400° C. with a flow of air at 5 L/min. Flow of air was continued for 120 min. Upon exit from the heated furnace, the formed metathesis and isomerization catalyst was collected in a filter. A total of 902 mg of metathesis and isomerization catalyst was collected from the filter.

The metathesis and isomerization catalyst was wet impregnated with $WO_3$ by adding 220 mg of the metathesis and isomerization catalyst collected in the filter to 23 mg of ammonium metatungstate and 2 ml of water in a 2 dram vial. The vial was rolled at 15 rotations per minute (rpm) for 2 hours. Subsequently, the solution was heated open to the atmosphere to 85° C. for 16 hours (h) to dry. The resulting silica substrate with the ammonium metatungstate was then calcined in a furnace at 550° C. for 480 min. A total of 120 mg of the resulting $WO_3$ impregnated metathesis and isomerization catalyst was collected from the furnace for catalytic testing.

Example 4—Aerosolized 80% Silica and 20% Alumina with 2 wt. % $WO_3$

A precursor was prepared from 12.0 g fumed silica, 22.2 g aluminum nitrate, 0.329 g ammonium metatungstate, and 570 ml water. The precursor was provided to an ultrasonic nebulizer at 21 ml/min unit aerosol flow was observed. Subsequently, the flow of precursor to the ultrasonic nebulizer was reduced to 1 ml/min for 120 min. The aerosolized precursor was transferred to a heated furnace at 1000° C. with a flow of air at 5 L/min. Flow of air was continued for 120 min. Upon exit from the heated furnace, the formed metathesis and isomerization catalyst was collected in a filter. A total of 221 mg of metathesis and isomerization catalyst was collected.

The performance of each of the example metathesis and isomerization catalysts were tested in a fixed bed reactor via the conversion of a stream of 2-butene to propylene. The fixed-bed flow reactor system had a quartz tube with a bed of metathesis and isomerization catalyst disposed between layers of quartz wool. Each of the metathesis and isomerization catalysts to be tested was serially mounted in the quartz tube as the bed of metathesis and isomerization catalyst disposed between the layers of quartz wool. Each metathesis and isomerization catalyst was tested sequentially to provide performance data for each metathesis and isomerization catalyst. The metathesis and isomerization catalyst was first activated at 550° C. under nitrogen flow at 0.025 liters/minute (l/min) for 1 hour. At the desired reaction temperature (550° C.), 2-butene was introduced into the reactor to start the reaction. The reaction was performed at 550° C. and at a space velocity of 4.2 $s^{-1}$, using nitrogen as a diluent. The flow stream exiting the fixed bed flow reactor was sent to a gas chromatograph for analysis of the product stream. The conversion of the 2-butene to reaction products and the percentage of propylene selectivity are provided subsequently in Table 1. Table 1 provides an average percent conversion and percent propylene selectivity for multiple experimental runs.

TABLE 1

| Catalyst | Catalyst Formation | Silica Wt. % in Support | Alumina Wt. % in Support | Nominal $WO_3$ Wt. % Added to Support | Average % Conversion | Average % Propylene Selectivity |
| --- | --- | --- | --- | --- | --- | --- |
| Example 1 | Aerosol | 100 | 0 | 2 (Aerosol) | 85.6 | 66.6 |
| Example 2 | Aerosol | 100 | 0 | 2 (Aerosol) | 82.8 | 63.3 |
| Example 3 | Aerosol | 100 | 0 | 10 (Wet Impregnation) | 81.2 | 21.5 |
| Example 4 | Aerosol | 80 | 20 | 2 (Aerosol) | 51.2 | 11.5 |
| Sigma Aldrich - Grade 135 | — | 93.5 | 6.5 | 10 (Wet Impregnation) | 54.4 | 18.1 |

Figure 2A:
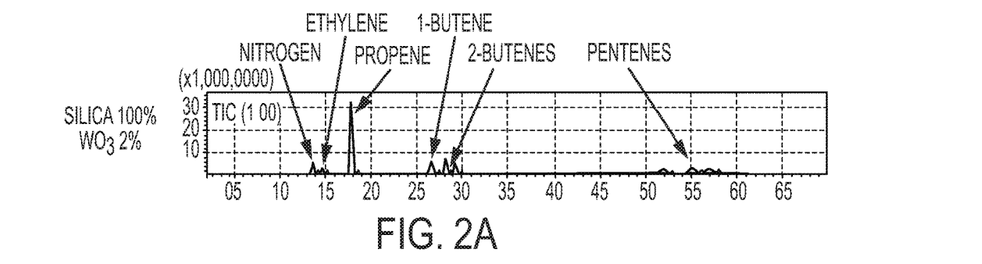
FIGS. 2A-2C are sample gas chromatographs for tested metathesis and isomerization catalysts formed in accordance with one or more embodiments of the present disclosure.
Figure 2B:
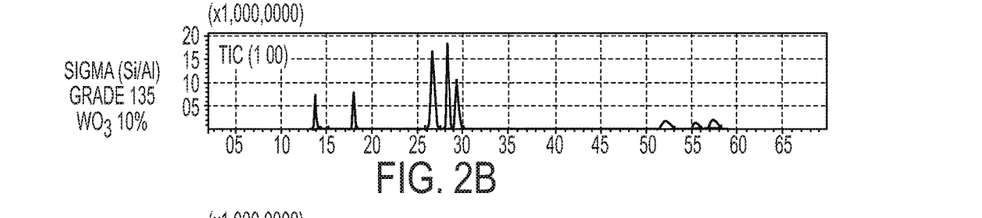
Figure 2C:
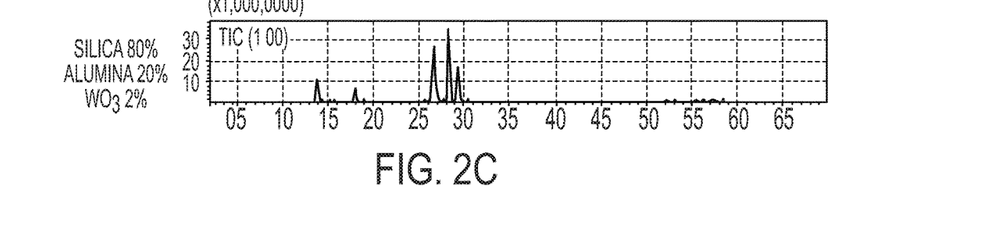

The percent conversion and percent propylene selectivity were determined by performing calculations with the integrated the area of butenes, integrated area of propylene, and the integrated area of all products in the gas chromatograph output. Specifically, percent conversion was calculated as the integrated area of butenes divided by the integrated area of products. Similarly, the percent propylene selectivity was calculated as the integrated area of products divided by the integrated are of propylene. The gas chromatograph results may be seen for Example 2 in FIG. 2A, Sigma Aldrich—Grade 135 with 10 wt. % wet impregnated WO₃ in FIG. 2B, and Example 4 in FIG. 2C.

Figure 3:
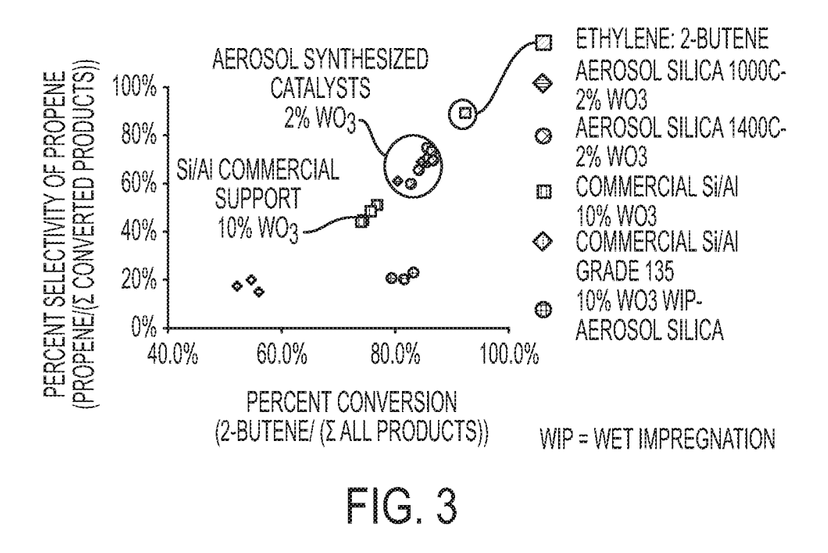
FIG. 3 is a graph illustrating the metathesis of 2-butene using a plurality of catalysts.

FIG. 3 illustrates the improved performance of the metathesis and isomerization catalyst formed from aerosol processing. Aerosolized silica with 2 wt. % WO₃ processed at both 1400° C. (Example 1) and 1000° C. (Example 2) in the heated furnace in accordance with this disclosure exhibit increased activity and selectivity of propylene in comparison to metathesis and isomerization catalysts formed from conventional methods. Specifically, an aerosolized silica which utilized wet impregnation to add 10 wt. % WO₃ exhibits a lower selectivity toward propylene. Further, a commercial Si/Al support with 10 wt. % WO₃ exhibits a lower selectivity and propylene as well as a lower conversion of 2-butene in comparison to metathesis and isomerization catalysts formed in accord with this disclosure. Finally, commercially available Si/Al grade 135 with no WO₃ exhibits a much lower percent conversion of 2-butene and a significant reduction in selectivity toward propylene.

The performance of each of the example metathesis and isomerization catalysts was tested using an alternate method as well. The metathesis and isomerization catalyst was pelletized with approximately 200 mg of catalyst and 180 mg of SiC. The pellets had heights ranging from 1.95 mm to 3.65 mm and weights of 297 mg to 369 mg. The pellets were placed into a stainless steel fitting and a stream comprising 2-butene was flowed through the pellet for conversion to propylene. The metathesis and isomerization catalyst was first activated at 550° C. under nitrogen flow at 5 ml/min for 1 h. At the desired reaction temperature (550° C.), a feed stream of a commercially available mixture of 10% trans-2-butene and 90% nitrogen was introduced into the reactor to start the reaction. The feed stream was provided at 5 ml/min for 3 to 6 h before data collection to condition the metathesis and isomerization catalyst. The flow stream exiting the fixed bed flow reactor was sent to a gas chromatograph for analysis of the product stream. The conversion of the 2-butene to reaction products and the percentage of propylene selectivity are provided subsequently in Table 2 for catalysts formed by aerosolization in accordance with this disclosure.

TABLE 2

| Catalyst | Silica Wt. % in Support | Alumina Wt. % in Support | Nominal WO₃ Wt. % Added to Support (Aerosolized) | Average % Conversion | Average % Propylene Selectivity | Propylene Yield Normalized for Pellet Size |
|---|---|---|---|---|---|---|
| Sample 1 | 95 | 5 | 10 | 68.35 | 37.61 | 24.16 |
| Sample 2 | 98 | 2 | 10 | 66.63 | 35.78 | 22.28 |
| Sample 3 | 98 | 2 | 10 | 71.24 | 37.42 | 25.05 |
| Sample 4 | 100 | 0 | 10 | 61.19 | 40.46 | 22.30 |
| Sample 5 | 100 | 0 | 10 | 64.38 | 40.52 | 22.28 |
| Sample 6 | 100 | 0 | 10 | 66.46 | 43.39 | 24.78 |
| Sample 7 | 100 | 0 | 10 | 65.20 | 42.70 | 25.13 |
| Sample 8 | 100 | 0 | 15 | 67.00 | 39.80 | 26.98 |
| Sample 9 | 95 | 5 | 10 | 68.79 | 27.35 | 22.71 |

The percent conversion and percent propylene selectivity were determined in the same manner as supra. Additionally, normalized propylene yield was calculated based on a target metathesis catalyst weight of 200 milligrams (mg) within the pellet. The normalized propylene yield was then able to be calculated according to Propene Selectivity/(pellet weight/200) to yield the propylene yield normalized to a 200 mg pellet.

Samples 1, 2, 4, and a benchmark standard were testing using yet a further technique. The benchmark standard was a 100% silica substrate (Cariact Q-10, Fuji Silysia Chemical Ltd.) impregnated by an incipient wetness technique with 10 wt. % WO₃. The metathesis and isomerization catalyst was pelletized with approximately 200 mg of catalyst and 180 mg of SiC. The pellets had heights ranging from 1.95 mm to 3.65 mm and weights of 297 mg to 369 mg. The pellets were placed into a stainless steel fitting and a stream comprising 2-butene was flowed through the pellet for conversion to propylene. The metathesis and isomerization catalyst was first activated at 550° C. under nitrogen flow at 5 ml/min for 2 h. At the desired initial reaction temperature (450° C.), a feed stream of a commercially available mixture of 10% trans-2-butene and 90% nitrogen was introduced into the reactor to start the reaction. The feed stream was provided at 5 ml/min for 3 to 6 h before data collection to condition the metathesis and isomerization catalyst. Data was collected at 450° C. for 250 minutes for the benchmark and 150 minutes for samples 1, 2, and 4 before ramping up to 500° C. at 5 C/min followed by data collection at 500° C. for 250 minutes or 150 minutes before ramping up to 550° C. at 1.7 C/min, and followed by data collection at 550° C. for 250 minutes or 150 minutes before ramping down to 450° C. at 3.3 C/min for data collection for 250 minutes or 150 minutes at 450° C. for a second time. The temperatures were held for 250 minutes or 150 minutes for the benchmark and samples 1, 2, and 4 respectively because of the time necessary to obtain 5 gas chromatography measurements. The benchmark standard was tested in a BTRS reactor and samples 1, 2, and 4 were tested in a PID reactor. The data obtained from each reactor is believed to be within +/−1% of the other. The flow stream exiting each fixed bed flow reactor was sent to a gas chromatograph for analysis of the product stream. The conversion of the 2-butene to reaction products and the percentage of ethylene, propylene, pentenes, and hexenes/C₆₊ selectivity are provided subsequently in Tables 3-6 and Tables 7-8.

TABLE 3

Benchmark Standard - 100% Silica with 10 wt. % $WO_3$ via Incipient Wetness Impregnation

| Unit | Temp. ° C. | Conversion | Ethylene | Propylene | Pentenes | Hexenes/$C_{6+}$ |
|---|---|---|---|---|---|---|
| BTRS | 450 | 47 | 0.5 | 14 | 17 | 3 |
|  | 500 | 62 | 2 | 21 | 21 | 7 |
|  | 550 | 72 | 4 | 28 | 19 | 8 |
|  | 450 | 39 | 0 | 12 | 16 | 2 |

TABLE 4

Sample 4 (100% Silica)

| Unit | Temp. ° C. | Conversion | Ethylene | Propylene | Pentenes | Hexenes/$C_{6+}$ |
|---|---|---|---|---|---|---|
| PID | 450 | 76 | 4 | 26 | 21 | 7 |
|  | 500 | 77 | 5 | 27 | 20 | 6 |
|  | 550 | 78 | 6 | 30 | 17 | 5 |
|  | 450 | 65 | 2 | 22 | 22 | 7 |

TABLE 5

Sample 1 (98% Silica; 2% Alumina)

| Unit | Temp. ° C. | Conversion | Ethylene | Propylene | Pentenes | Hexenes/$C_{6+}$ |
|---|---|---|---|---|---|---|
| PID | 450 | 78 | 4 | 26 | 22 | 5 |
|  | 500 | 78 | 5 | 27 | 21 | 6 |
|  | 550 | 75 | 5 | 26 | 19 | 5 |
|  | 450 | 63 | 2 | 19 | 21 | 6 |

TABLE 6

Sample 2 (95% Silica; 5% Alumina)

| Unit | Temp. ° C. | Conversion | Ethylene | Propylene | Pentenes | Hexenes/$C_{6+}$ |
|---|---|---|---|---|---|---|
| PID | 450 | 79 | 4 | 26 | 21 | 6 |
|  | 500 | 79 | 5 | 27 | 21 | 7 |
|  | 550 | 77 | 5 | 28 | 18 | 6 |
|  | 450 | 69 | 2 | 23 | 20 | 6 |

TABLE 7

Propylene Selectivity (wt. %)

|  | 450° C. | 500° C. | 550° C. | 450° C. |
|---|---|---|---|---|
| Benchmark | 14 | 21 | 28 | 12 |
| Sample 4 | 26 | 27 | 30 | 22 |
| Sample 2 | 26 | 27 | 28 | 23 |
| Sample 1 | 26 | 27 | 26 | 19 |

TABLE 8

Conversion (%)

|  | 450° C. | 500° C. | 550° C. | 450° C. |
|---|---|---|---|---|
| Benchmark | 47 | 62 | 72 | 39 |
| Sample 4 | 76 | 77 | 78 | 65 |
| Sample 2 | 79 | 79 | 77 | 69 |
| Sample 1 | 78 | 78 | 75 | 63 |

As shown in Tables 7 and 8, the conversion and propylene selectivity of samples 1, 2 and 4 are superior to the Benchmark sample at 450° C. Further, the mild superiority of the conversion and propylene selectivity of samples 1, 2, and 4 over the Benchmark sample is also evident at 500° C. and 550° C.

It should now be understood that various aspects of the systems and methods of making catalytic materials via aerosol processing are described and such aspects may be utilized in conjunction with various other aspects.

In a first aspect, the disclosure provides a method of synthesizing a metathesis and isomerization catalyst. The method comprises forming a catalyst precursor mixture comprising a diluent and a catalyst precursor. The catalyst precursor comprising an oxometallate precursor or a metal oxide precursor and at least one of an alumina precursor and a silica precursor. The catalyst precursor solution is absent a surfactant. The method also includes aerosolizing the catalyst precursor mixture and drying the aerosolized catalyst precursor mixture to form a dried catalyst precursor. Further, the method includes reacting the dried catalyst precursor to yield the metathesis and isomerization catalyst, the metathesis and isomerization catalyst comprising a silica or silica and alumina support with an oxometallate or metal oxide distributed within the silica or silica and alumina support.

In a second aspect, the disclosure provides a method of synthesizing an isomerization catalyst. The method comprises forming a catalyst precursor mixture comprising a diluent and a catalyst precursor. The catalyst precursor comprising a silica precursor and an alumina precursor, where the catalyst precursor solution is absent a surfactant. The method also includes aerosolizing the catalyst precursor mixture and drying the aerosolized catalyst precursor mixture to form a dried catalyst precursor. Further, the method includes reacting the dried catalyst precursor to yield the isomerization catalyst, the isomerization catalyst comprising a silica and alumina support.

In a third aspect, the disclosure provides a method of synthesizing a metathesis catalyst, The method comprises forming a catalyst precursor mixture comprising a diluent and a catalyst precursor. The catalyst precursor comprising an oxometallate precursor or a metal oxide precursor and at least one of an alumina precursor and a silica precursor. The catalyst precursor mixture is absent a surfactant. The method also includes aerosolizing the catalyst precursor mixture and drying the aerosolized catalyst precursor mixture to form a dried catalyst precursor. Further, the method includes reacting the dried catalyst precursor to yield the metathesis catalyst, the metathesis catalyst comprising a silica or silica and alumina support with an oxometallate or metal oxide distributed within the silica or silica and alumina support.

In a fourth aspect, the disclosure provides a method of any of the first through third aspects in which the silica precursor comprises fumed silica.

In a fifth aspect, the disclosure provides a method of any of the first through fourth aspects in which the catalyst precursor comprises the oxometallate precursor.

In a sixth aspect, the disclosure provides a method of the fifth aspect in which the oxometallate precursor comprises a tungstate precursor.

In a seventh aspect, the disclosure provides a method of the sixth aspect in which the tungstate precursor comprises ammonium metatungstate.

In an eighth aspect, the disclosure provides a method of any of the first through fourth aspects in which the catalyst precursor comprises the metal oxide precursor.

In a ninth aspect, the disclosure provides a method of any of the first to eighth aspects in which the alumina precursor comprises aluminum nitrate.

In a tenth aspect, the disclosure provides a method of any of the first to ninth aspects in which the catalyst precursor comprises 0.1-99.9 wt. % silica precursor, 0.1-20 wt. % oxometallate precursor or metal oxide precursor, and 0.0-99.8 wt. % alumina precursor.

In an eleventh aspect, the disclosure provides a method of any of the first to tenth aspects in which the catalyst precursor mixture is aerosolized in a nebulizing unit.

In a twelfth aspect, the disclosure provides a method of any of the first to eleventh aspects in which the diluent is water.

In an thirteenth aspect, the disclosure provides a method of the twelfth aspect in which the catalyst precursor mixture is aerosolized at a catalyst precursor concentration of between 1 wt. % and 20 wt. %.

In a fourteenth aspect, the disclosure provides a method of the twelfth aspect in which the catalyst precursor mixture is aerosolized at a catalyst precursor concentration of between 1 wt. % and 6 wt. %.

In a fifteenth aspect, the disclosure provides a method of any of the first to fourteenth aspects in which drying the aerosolized catalyst precursor mixture comprises providing a flow of a carrier gas through the aerosolized catalyst precursor mixture and into a heated furnace to transport the aerosolized precursor into the heated furnace.

In a sixteenth aspect, the disclosure provides a method of the fifteenth in which the carrier gas is air.

In a seventeenth aspect, the disclosure provides a method of any of the first to sixteenth aspects in which the furnace is heated to between 500 and 1500° C.

In an eighteenth aspect, the disclosure provides a method of any of the first to seventeenth aspects in which the furnace is heated to between 1000 and 1500° C.

In a nineteenth aspect, the disclosure provides a method of any of the first to eighteenth aspects in which the residence time in the heated furnace is between 0.1 and 60 seconds.

In a twentieth aspect, the disclosure provides a method of any of the first to nineteenth aspects in which the method further comprises collecting the metathesis and isomerization catalyst with a filter from the flow of the carrier gas exiting the heated furnace.

In a twenty-first aspect, the disclosure provides a method of any of the first to twentieth aspects in which the catalyst precursor mixture comprises at least one of titania, rhenia, ceria, or a phosphate.

In a twenty-second aspect, the disclosure provides a method of any of the first to twenty-first aspects in which the method further comprises aerosolizing a dopant stream concurrently with aerosolizing the catalyst precursor mixture.

In a twenty-third aspect, the disclosure provides a method of the twenty-second aspect in which the dopant stream comprises at least one of titania, rhenia, ceria, or a phosphate.

In a twenty-fourth aspect, the disclosure provides a method of any of the first to twenty-third aspects in which the metathesis and isomerization catalyst has a surface area of 100 to 700 $m^2/g$.

Throughout this disclosure ranges are provided for various processing parameters and characteristics of the metathesis and isomerization catalyst, metathesis catalyst, or isomerization catalyst. It will be appreciated that when one or more explicit ranges are provided the individual values and the ranges formed therebetween are also intended to be provided as providing an explicit listing of all possible combinations is prohibitive. For example, a provided range of 1-10 also includes the individual values, such as 1, 2, 3, 4.2, and 6.8, as well as all the ranges which may be formed within the provided bounds, such as 1-8, 2-4, 6-9, and 1.3-5.6.

It should be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

What is claimed is:

1. A method of synthesizing a metathesis and isomerization catalyst, the method comprising:

forming a catalyst precursor mixture comprising a diluent and a catalyst precursor, the catalyst precursor comprising an oxometallate precursor or a metal oxide precursor and at least one of an alumina precursor and a silica precursor, where the catalyst precursor mixture is absent a surfactant;

aerosolizing the catalyst precursor mixture;

drying the aerosolized catalyst precursor mixture to form a dried catalyst precursor, where drying the aerosolized catalyst precursor mixture comprises providing a flow of a carrier gas through the aerosolized catalyst precursor mixture and into a heated furnace to transport the aerosolized precursor into the heated furnace; and thermally decomposing the dried catalyst precursor to yield the metathesis and isomerization catalyst, the metathesis and isomerization catalyst comprising a silica or silica and alumina support with an oxometallate or metal oxide distributed within the silica or silica and alumina support, where the furnace is heated to between 500 and 1500° C.

2. The method of claim 1 where the silica precursor comprises fumed silica.

3. The method of claim 1 where the catalyst precursor comprises the oxometallate precursor.

4. The method of claim 3 where the oxometallate precursor comprises a tungstate precursor.

5. The method of claim 4 where the tungstate precursor comprises ammonium metatungstate.

6. The method of claim 1 where the catalyst precursor comprises the metal oxide precursor.

7. The method of claim 1 where the alumina precursor comprises aluminum nitrate.

8. The method of claim 1 where the catalyst precursor comprises 0.1-99.9 wt. % silica precursor, 0.1-20 wt. % oxometallate precursor or metal oxide precursor, and 0.0-99.8 wt. % alumina precursor.

9. The method of claim 1 where the catalyst precursor mixture is aerosolized in a nebulizing unit.

10. The method of claim 1 where the diluent is water.

11. The method of claim 10 where the catalyst precursor mixture is aerosolized at a catalyst precursor concentration of between 1 wt. % and 20 wt. %.

12. The method of claim 10 where the catalyst precursor mixture is aerosolized at a catalyst precursor concentration of between 1 wt. % and 6 wt. %.

13. The method of claim 1 where the carrier gas is air.

14. The method of claim 1 where the furnace is heated to between 1000 and 1500° C.

15. The method of claim 1 where the residence time in the heated furnace is between 0.1 and 60 seconds.

16. The method of claim 1 where the method further comprises collecting the metathesis catalyst and the isomerization catalyst with a filter from the flow of the carrier gas exiting the heated furnace.

17. The method of claim 1 where the catalyst precursor mixture comprises at least one of titania, ceria, rhenia, or a phosphate.

18. The method of claim 1 where the method further comprises aerosolizing a dopant stream concurrently with aerosolizing the catalyst precursor mixture.

19. The method of claim 18 where the dopant stream comprises at least one of titania, ceria rhenia, or a phosphate.

20. The method of claim 1 where the metathesis and isomerization catalyst has a surface area of 100 to 700 m$^2$/g.

21. A method of synthesizing an isomerization catalyst, the method comprising:

forming a catalyst precursor mixture comprising a diluent and a catalyst precursor, the catalyst precursor comprising a silica precursor and an alumina precursor, where the catalyst precursor solution is absent a surfactant;

aerosolizing the catalyst precursor mixture;

drying the aerosolized catalyst precursor mixture to form a dried catalyst precursor, where drying the aerosolized catalyst precursor mixture comprises providing a flow of a carrier gas through the aerosolized catalyst precursor mixture and into a heated furnace to transport the aerosolized precursor into the heated furnace; and thermally decomposing the dried catalyst precursor to yield the isomerization catalyst, the isomerization catalyst comprising a silica and alumina support, where the furnace is heated to between 500 and 1500° C.

22. A method of synthesizing a metathesis catalyst, the method comprising:

forming a catalyst precursor mixture comprising a diluent and a catalyst precursor, the catalyst precursor comprising an oxometallate precursor or a metal oxide precursor and at least one of an alumina precursor and a silica precursor, where the catalyst precursor mixture is absent a surfactant;

aerosolizing the catalyst precursor mixture;

drying the aerosolized catalyst precursor mixture to form a dried catalyst precursor, where drying the aerosolized catalyst precursor mixture comprises providing a flow of a carrier gas through the aerosolized catalyst precursor mixture and into a heated furnace to transport the aerosolized precursor into the heated furnace; and thermally decomposing the dried catalyst precursor to yield the metathesis catalyst, the metathesis catalyst comprising a silica or silica and alumina support with an oxometallate or metal oxide distributed within the silica or silica and alumina support, where the furnace is heated to between 500 and 1500° C.

* * * * *